US012734348B2

(12) United States Patent
Damarati

(10) Patent No.: US 12,734,348 B2
(45) Date of Patent: Sep. 15, 2026

(54) MEDICAL CONNECTOR CONNECTION SYSTEM

(71) Applicant: NP Medical Inc., Clinton, MA (US)

(72) Inventor: John Damarati, Marlborough, MA (US)

(73) Assignee: NP MEDICAL INC., Clinton, MA (US)

( * ) Notice: Subject to any disclaimer, the term of this patent is extended or adjusted under 35 U.S.C. 154(b) by 1474 days.

(21) Appl. No.: 17/269,700

(22) PCT Filed: Sep. 4, 2019

(86) PCT No.: PCT/US2019/049442
§ 371 (c)(1),
(2) Date: Feb. 19, 2021

(87) PCT Pub. No.: WO2020/051179
PCT Pub. Date: Mar. 12, 2020

(65) Prior Publication Data
US 2021/0196940 A1 Jul. 1, 2021

Related U.S. Application Data

(60) Provisional application No. 62/726,630, filed on Sep. 4, 2018.

(51) Int. Cl.
*A61M 39/10* (2006.01)
*A61M 25/00* (2006.01)
*A61M 25/02* (2006.01)

(52) U.S. Cl.
CPC ........ *A61M 39/10* (2013.01); *A61M 25/0097* (2013.01); *A61M 2025/0266* (2013.01); *A61M 2205/3303* (2013.01); *A61M 2207/00* (2013.01)

(58) Field of Classification Search
CPC .............. A61M 39/10; A61M 39/1011; A61M 39/1016; A61M 2207/00;
(Continued)

(56) References Cited

U.S. PATENT DOCUMENTS 3,628,813 A * 12/1971 Lee, Jr. ................. A61M 39/10 285/364
4,082,094 A * 4/1978 Dailey ............... A61M 39/1011 604/93.01
(Continued)

FOREIGN PATENT DOCUMENTS

CN 109999333 A * 7/2019 ........... A61M 39/10
WO WO-2010033858 A1 * 3/2010 ........... A61M 25/02
(Continued)

OTHER PUBLICATIONS

International Search Report and Written Opinion for Application No. PCT/US2019/049442, dated Dec. 13, 2019, 11 pages.

*Primary Examiner* — Bhisma Mehta
*Assistant Examiner* — Mark A Igel
(74) *Attorney, Agent, or Firm* — McCarter & English, LLP; Jonathan C. Lovely

(57) ABSTRACT

A method fluidly connects a male luer connector and a female luer connector. To that end, a housing having a first end and a second end is provided. The housing has a first opening nearer to the first end that is configured to receive the male luer connector. The housing also includes a second opening nearer to the second end that is configured to receive the female luer connector. The male luer connector is positioned into the first opening in a direction that is along a central axis of the housing. The female luer connector is positioned into the second opening in a direction that is transverse to a central axis of the housing. The method then advances the male luer connector into the opening of the
(Continued)

female luer connector so as to form a fluid connection therebetween.

13 Claims, 10 Drawing Sheets

(58) Field of Classification Search
CPC .. A61M 2205/3303; A61M 2025/0266; A61M 25/0097
See application file for complete search history.

(56) References Cited

U.S. PATENT DOCUMENTS 4,250,880 A * 2/1981 Gordon ................ A61M 25/02 128/DIG. 26
4,617,012 A * 10/1986 Vaillancourt ......... A61M 39/10 604/905
4,997,421 A * 3/1991 Palsrok ............. A61M 39/1011 604/174
5,314,411 A * 5/1994 Bierman ........... A61M 39/1011 604/174
2001/0047154 A1* 11/2001 Jepson .................. A61M 39/14 604/167.01
2007/0179446 A1* 8/2007 Carrez ............. A61M 25/0606 604/164.08
2009/0024090 A2* 1/2009 Wright .................. A61M 25/02 604/174
2009/0292273 A1* 11/2009 Racz ................. A61M 25/0097 604/533
2013/0338644 A1* 12/2013 Solomon ............. A61M 39/162 604/535
2014/0276542 A1* 9/2014 Ciccone ................ A61M 25/02 604/178
2017/0326340 A1* 11/2017 Howell ................. A61M 25/02
2019/0388672 A1* 12/2019 Mcneal .................. A61B 1/125
2020/0086088 A1* 3/2020 Augustine ............. A61M 25/02
2020/0330733 A1* 10/2020 Howell ................. A61M 25/02
2021/0283375 A1* 9/2021 Spitler .................. A61M 25/02
2024/0293654 A1* 9/2024 Densley ................ A61M 39/12
2024/0424279 A1* 12/2024 Feith ................. A61M 39/1055

FOREIGN PATENT DOCUMENTS

WO WO-2011038045 A2 * 3/2011 ............ A61M 5/158
WO 2012/048133 A2 4/2012

* cited by examiner 89
40
85
120
90
69
70
73
71
65
115
87

87
130
122
115
55
85
120
70
130
65
130

MEDICAL CONNECTOR CONNECTION SYSTEM

PRIORITY

This patent application is a 35 U.S.C. § 371 national stage filing of International Application No. PCT/US2019/049442, filed on Sep. 4, 2019, which claims priority from U.S. Provisional Patent Application No. 62/726,630, filed on Sep. 4, 2018, entitled, "Medical Connector Connection System," and naming John Damarati as inventor. The disclosure of each of the foregoing applications is incorporated herein, in its entirety, by reference.

FIELD OF THE INVENTION

Illustrative embodiments of the invention generally relate to medical connectors and, more particularly, illustrative embodiments relate to an apparatus for connecting luer connectors.

BACKGROUND OF THE INVENTION

Many patient fluid transfer applications require a medical practitioner to administer fluid to or take a sample of blood or fluid from the patient through an indwelling catheter. To that end, the practitioner typically uses a fluid transfer set having a sample port that allows the medical practitioner to deliver to or draw a sample of the blood or fluid from the patient's indwelling catheter.

In general terms, medical connectors, such as valving devices, often act as a port that may be repeatedly accessed to non-invasively inject fluid into (or withdraw fluid from) a patient's vasculature. Consequently, a medical connector permits the patient's vasculature to be freely accessed without requiring the patient's skin to be repeatedly pierced by a needle. Alternatively, medical connectors may act as a port for other medical applications, such as for accessing fluid containers (e.g., bags, vials), trachea tubes, enteral lines, breathing apparatuses, surgical sites, etc.

Medical personnel insert a medical instrument into the medical connector to inject fluid into (or withdraw fluid from) a patient who has an appropriately secured medical connector. Once inserted, fluid may be freely injected into or withdrawn from the patient.

SUMMARY OF VARIOUS EMBODIMENTS

In accordance with one embodiment of the invention, a method fluidly connects a male luer connector and a female luer connector. To that end, a housing having a first end and a second end is provided. The housing has a first opening nearer to the first end that is configured to receive the male luer connector. The housing also includes a second opening nearer to the second end that is configured to receive the female luer connector. The male luer connector is positioned into the first opening in a direction that is along a central axis of the housing. The female luer connector is positioned into the second opening in a direction that is transverse to a central axis of the housing. The method then advances the male luer connector into the opening of the female luer connector so as to form a fluid connection therebetween.

The housing may have a stop configured to prevent advancement of the male luer connector into an opening of the female luer connector. The stop is disengaged when the female luer connector is positioned into the second opening.

In some embodiments, the female luer connector is part of a catheter. Furthermore, the catheter may be inserted in a patient prior to fluidly connecting the male luer connector and the female luer connector. To that end, the housing may be integrated into a patch or a dressing. The patch or the dressing may include integrated biosensors and/or an adhesive portion.

The housing may include a biasing member configured to bias the male luer connector towards the second end so that the male luer connector is biased into fluid connection with the female luer connector when the stop is disengaged. The first opening may have a track that receives the male luer connector. In some embodiments, the track may be movable relative to the housing, and thus, advanced towards the second end along with the male luer connector.

In accordance with another embodiment, a housing fluidly connects a male luer connector and a female luer connector. The housing has a first end and a second end. The housing has an interior formed by a wall having a first opening nearer to the first end that is configured to receive the male luer connector. The male luer connector is positioned into the first opening in a direction that is along a central axis of the housing. The housing also includes a second opening (e.g., a slot) nearer to the second end. The second opening is configured to receive the female luer connector. The female luer connector is positioned into the second opening in a direction that is transverse to a central axis of the housing and/or transverse to a central axis of the female luer connector.

In some embodiments, the housing is configured so that insertion of the female luer connector into the second opening disengages a stop that prevents connection of the male luer connector and the female luer connector. Furthermore, the housing may include a biasing member that is configured to bias the male luer connector towards the second end. Thus, the male luer connector is biased into fluid connection with the female luer connector when the stop is disengaged. To that end, the housing may include a housing cap to bias the male luer connector against. The male luer connector may also include a push button.

In accordance with another embodiment, a catheter connection system includes a male luer connector, a female luer connector, and a housing for receiving the male luer connector and the female luer connector. The female luer connector may have an open end with a hub and a catheter end. The housing includes a first opening nearer to the first end that is configured to receive the male luer connector. The housing also includes a female luer connector receiving portion configured to receive the female luer connector. The hub of the female luer connector is positioned into the receiving portion in a direction that is transverse to a central axis of the housing.

The housing may be configured so that positioning the hub of the female luer connector into the female luer connector receive portion disengages a stop that prevents connection of the male luer connector and the female luer connector.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

DESCRIPTION OF ILLUSTRATIVE EMBODIMENTS

In illustrative embodiments, a medical practitioner fluidly connects a female luer and a male luer by coupling a housing to the female luer, in a direction transverse to the longitudinal axis of the female luer. In contrast, many prior art fluid connections require that the male luer be inserted axially (i.e., along the longitudinal axis of the female luer) into the female luer by the medical practitioner. Illustrative embodiments are advantageous in patch embodiments, especially in situations where visibility of the male luer connector is obscured from the perspective of the practitioner. Accordingly, illustrative embodiments provide simple one-handed fluid connection with catheters. Details of illustrative embodiments are discussed below.

Figure 1:
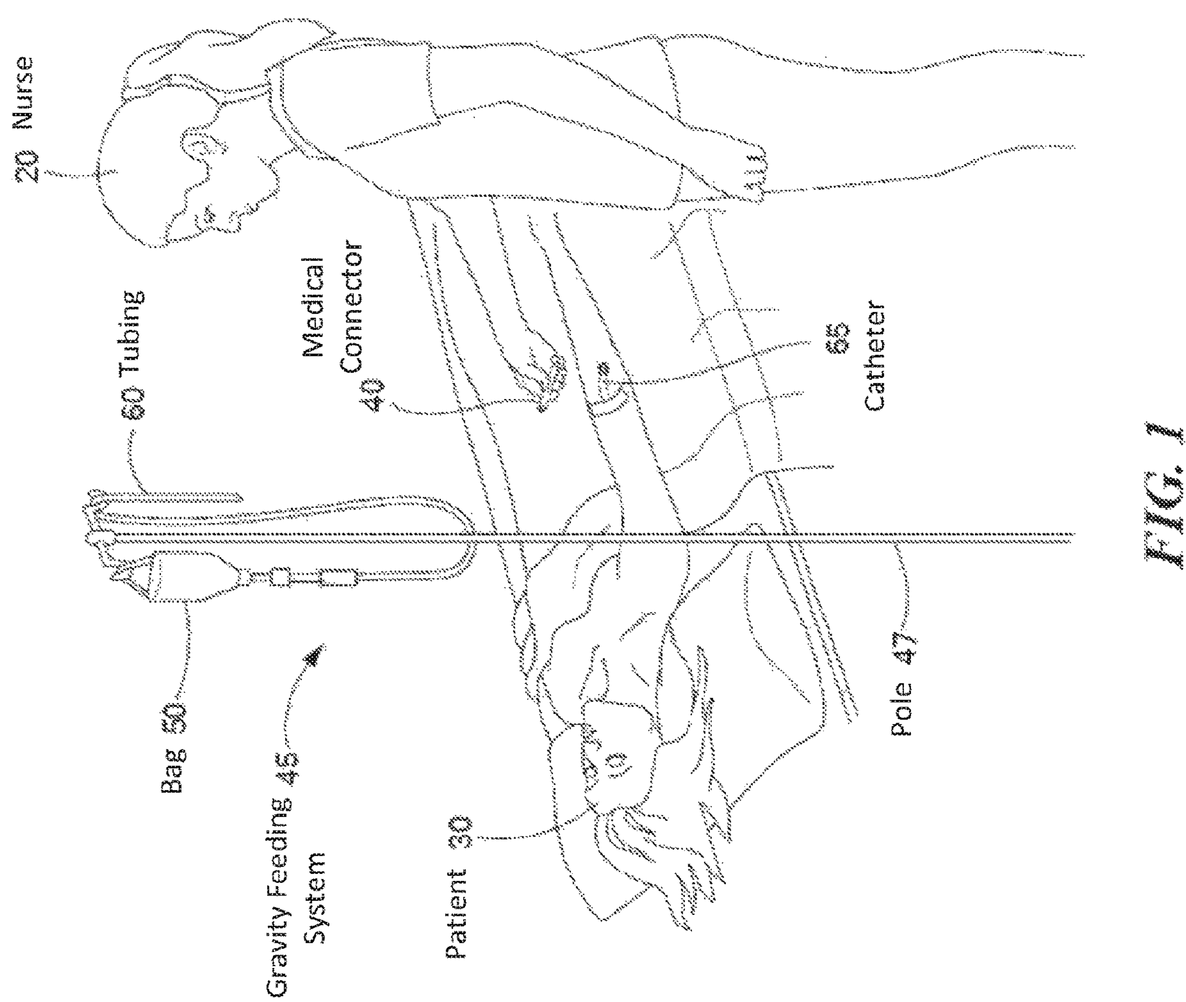
FIG. 1 schematically shows one illustrative use of a medical connector configured in accordance with illustrative embodiments of the invention.

FIG. 1 schematically shows one illustrative use of a medical connector 40 (e.g., a male luer connector 40) configured in accordance with illustrative embodiments of the invention. In this example, a catheter 65 connects the connector 40 with a patient's vein (the patient is identified by reference number 30). The catheter 65 has an open end 69 configured to receive the male luer connector 40. Adhesive tape or similar material may be coupled with the catheter 65 and the patient's 30 arm to ensure that the connector 40 remains in place.

After the connector 40 is in place, a nurse, doctor, technician, practitioner, or other user (schematically identified by reference number 20) may intravenously deliver medication to the patient 30, who is lying in a hospital bed. To that end, after the connector 40 is properly primed and flushed (e.g., with a saline flush), the nurse 20 swabs the top surface of the connector 40 to remove contaminants. Next, the nurse 20 uses a medical instrument (e.g., a syringe having a distally located blunt, luer tip complying with ANSI/ISO standards) to inject medication into the patient 30 through the connector 40. For example, the medical practitioner 20 may use the connector 40 to inject drugs such as heparin, antibiotic, pain medication, other intravenous medication, or other fluid deemed medically appropriate. Alternatively, the nurse 20 (or other user) may withdraw blood from the patient 30 through the connector 40.

The medical connector 40 may receive medication or other fluids from other means, such as through a gravity feed system 45. In general, traditional gravity feeding systems 45 often have a bag 50 (or bottle) containing a fluid (e.g., anesthesia medication) to be introduced into the patient 30. The bag 50 (or bottle) typically hangs from a pole 47 to allow for gravity feeding. The medical practitioner 20 then connects the bag/bottle 50 to the medical connector 40 using tubing 60 having an attached blunt tip. In illustrative embodiments, the blunt tip of the tubing 60 has a luer taper that complies with the ANSI/ISO standard. After the tubing 60 is connected to the medical connector 40, gravity (or a pump) causes the fluid to begin flowing into the patient 30. In some embodiments, the feeding system 45 may include shut-off devices on the tubing 60 (e.g., stop-cocks or clamps) to stop fluid flow without having to disconnect the tubing 60 from the connector 40. Accordingly, the connector 40 can be used in long-term "indwell" procedures.

In other medical applications, alternative access procedures are performed by medical personnel 20 for accessing fluid containers (e.g. bags, vials), trachea tubes, enteral lines, breathing apparatuses, surgical sites, etc. through the medical connector 40.

Figure 2:
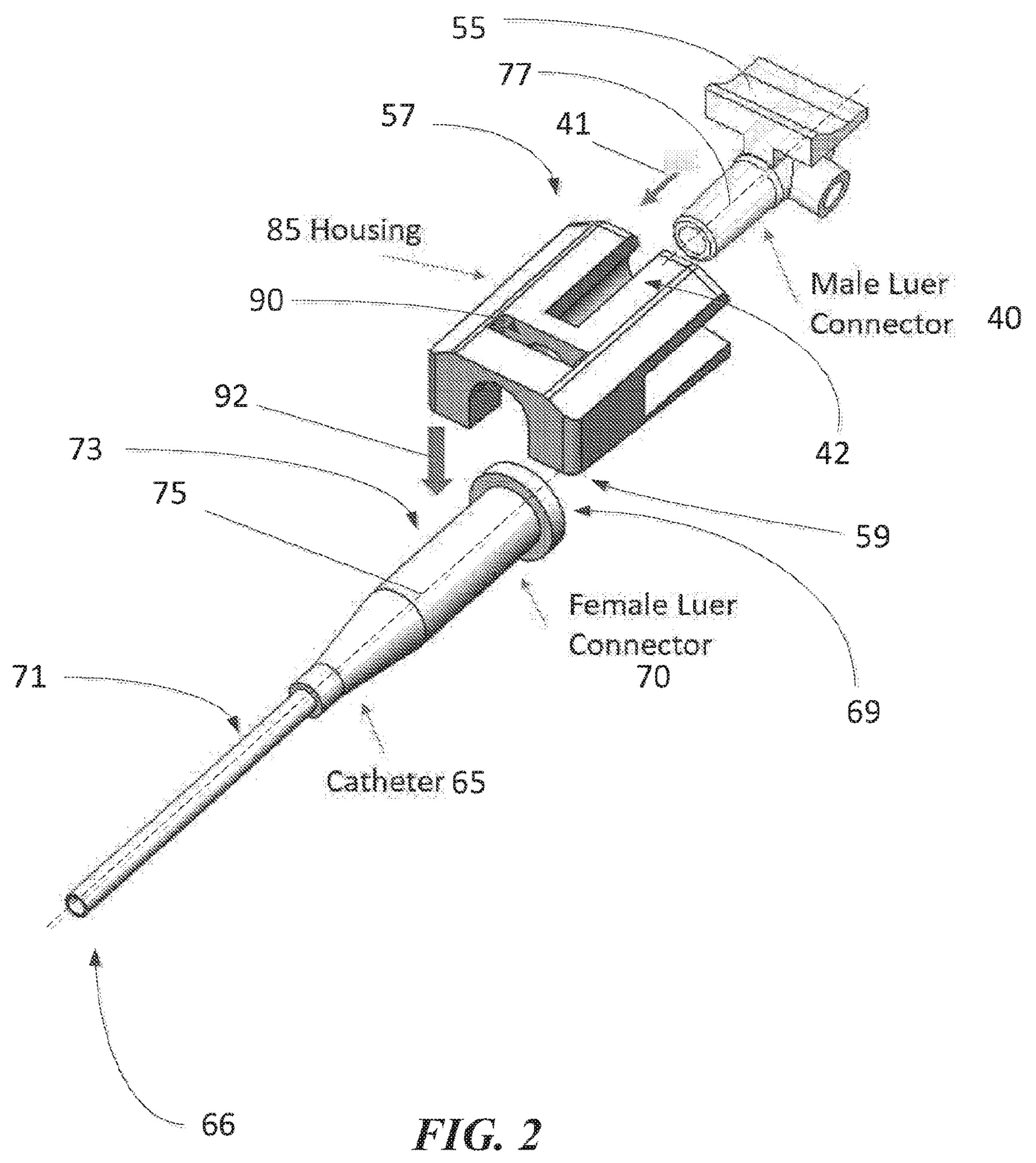
FIG. 2 schematically shows a perspective view of the housing prior to fluidly connecting the catheter and the male luer connector in accordance with illustrative embodiments of the invention.

FIG. 2 schematically shows a perspective view of a housing 85 configured to fluidly connect the catheter 65 and the male luer connector 40 in accordance with illustrative embodiments of the invention. The catheter 65 has a vein dwelling element 71, which although not shown as such in the figure, may have a distal end 66 inserted into the patient 30. The catheter 65 also has a hub 73, which may include a female luer connector 70, a lip 69, threads, etc.

As shown, the housing 85 may have a track 42, starting at a proximal housing end 57, configured to receive the male luer connector 40. The track 42 may be formed by the inner diameter of the housing 85. In some embodiments, not shown here, the track 42 may be movable relative to the rest of the housing 85. The male luer connector 40 may be moved along the track 42 from the retracted position to the engagement position. Illustrative embodiments describe how to position the male luer connector 40 into the housing using the track 42. The track 42 may have a funnel shape that guides the male luer connector 40.

The male luer connector 40 is aligned with an opening of the track 42 and, during use, a force is applied on the male luer connector 40 in a direction 41 towards a distal end 59 of the housing 58 along an axis that is parallel to a central axis 77 (e.g., along the central axis) of the male luer connector 40 (i.e., towards the opening of the female luer connector 70). Additionally, or alternatively, the male luer connector 40 may be advanced in the direction 41, which is parallel (e.g., along) a central axis of the housing 85. After the male luer connector 40 is positioned in the track 42, the connector 40 may be advanced towards the distal end 59 of the housing (e.g., towards the opening of the female luer connector 70). For example, the practitioner 20 may insert the male luer connector 40 into the track 42 and press on a thumb plate 55 of the connector 40. Alternatively, the male luer connector 40 may be assembled within the housing as a part of the manufacturing process. In some embodiments, the track 42, in addition to the connector 40, may be movable relative to the housing. Some embodiments include a stop (not shown in this figure) that prevents the male luer connector 40 from advancing farther into the housing 85 until the female luer connector 70 has been positioned in the housing 85.

In a manner similar to the male luer connector 40, the female luer connector 70 (and the catheter 65) has a central axis 75. Additionally, the female luer connector 70 has an opening (not directly visible from this view) that receives the male luer connector 40. Generally, to fluidly connect the female luer connector 70 and the male luer connector 40, a practitioner 20 aligns the central axis 77 of the male luer connector with the central axis 75 of the female luer connector 70, and then applies a force axially. Some connectors also require rotational force (e.g., engaging threads). Thus, using the housing 85, prior art male luer connectors 40 may be inserted and advanced directly into the opening of the female luer connector 70. Accordingly, when coupled, the housing 85 fluidly connects the female luer connector 70 and the male luer connector 40. Specifically, the male luer connector 40 advances along a track 42 directly into the opening of the female luer connector 70, which itself is coupled to the housing 85 using a motion that is in a direction 92 transverse to the central axis 75 of the housing 85. Additionally, or alternatively, in some embodiments, that direction 92 is also transverse to the central axis of the female luer connector 70.

Figure 3:
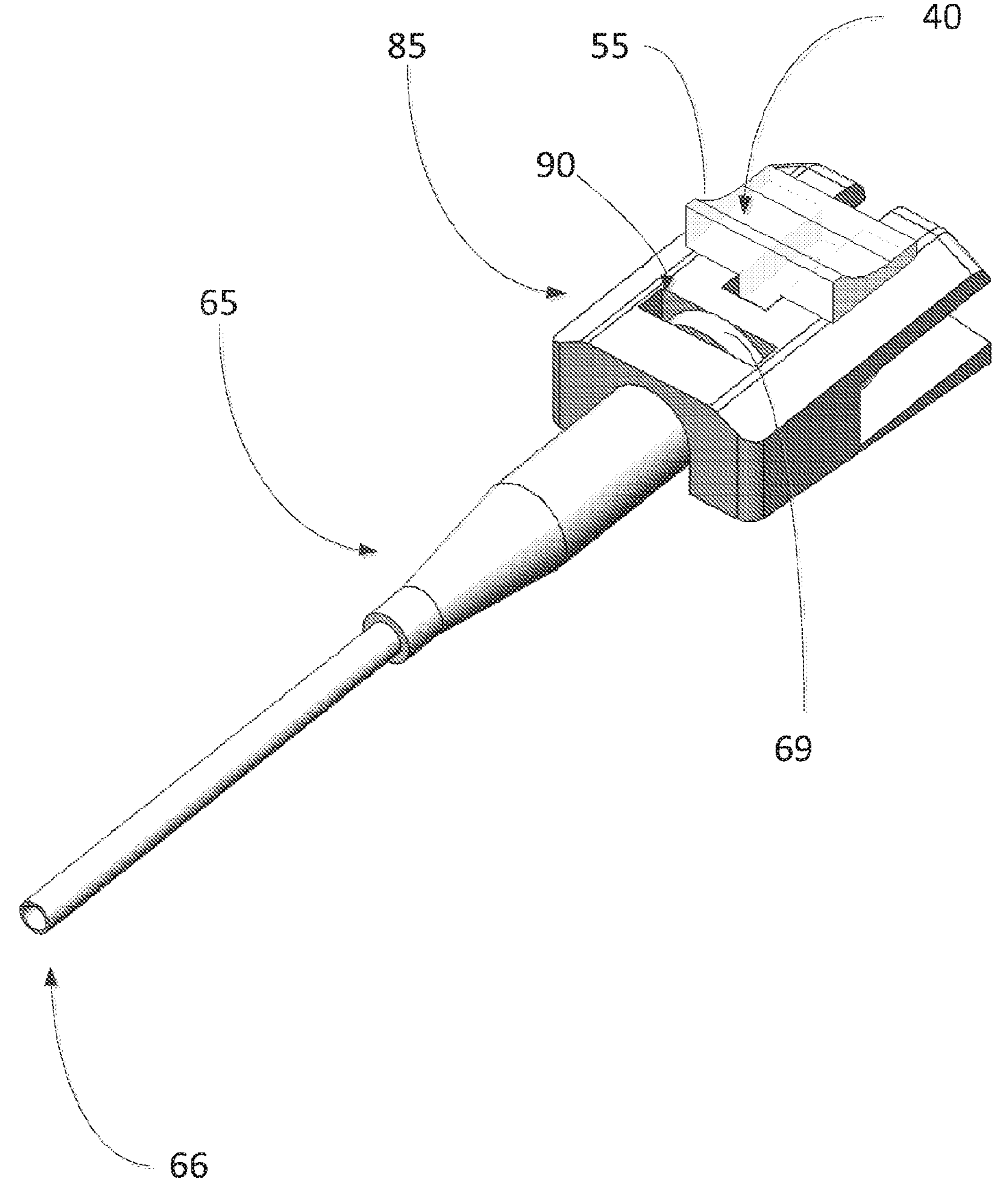
FIG. 3 schematically shows a perspective view of the housing of FIG. 2 used to fluidly connect the female luer connector and the male luer connector in accordance with illustrative embodiments of the invention.

FIG. 3 schematically shows a perspective view of the housing 85 while coupled with the female luer connector 70 and the male luer connector 40. While the male luer connector 40 is not directly visible in FIG. 2, the prior noted thumb plate 55, which may be part of the male luer connector 40, is visible. As shown, the housing 85 effectively fluidly connects the male luer connector 40 and the female luer connector 70.

As described previously, illustrative embodiments may include a stop that prevents the male luer connector 40 from being fully advanced into the housing 85. Positioning the female luer connector 70, or some other portion of the catheter 65 into the housing 85 may disengage the stop. For example, the female luer connector 70 (e.g., a lip 69 of the connector 70) may be positioned into a slot 90 of the housing 85, disengaging the stop. In illustrative embodiments, the female luer connector 70 is coupled to the housing 85 using a motion that is transverse to the central axis of the female luer connector 70.

Figure 4:
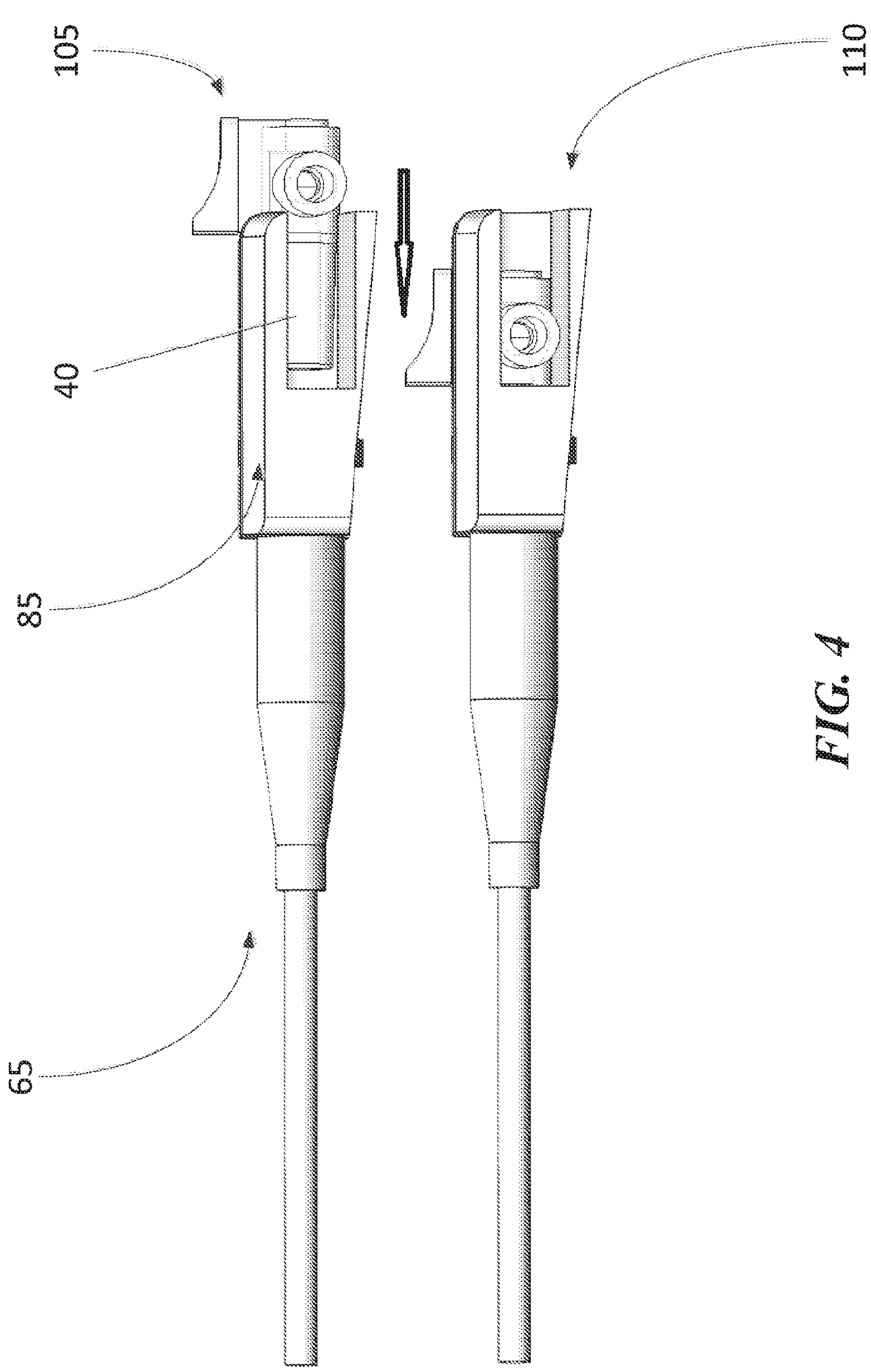
FIG. 4 schematically shows the male luer connector transitioning from a retracted position to an engagement position in accordance with illustrative embodiments of the invention.

FIG. 4 schematically shows the male luer connector 40 transitioning from a retracted position 105 to an engagement position 110 in accordance with illustrative embodiments of the invention. In the retracted position 105, the male luer connector 40 is positioned in the housing 85, but not advanced sufficiently to fluidly connect with the female luer connector 70 (luer connector 70 not visible because it is in the housing 85). However, when the female luer connector 70 is positioned in the housing 85, it disengages the stop. Accordingly, the male luer connector 40 may be advanced further into the female luer connector 70, thereby forming the fluid connection. In some embodiments, disengagement of the stop triggers insertion of the male luer connector 40 (e.g., the male luer connector 40 may be spring biased).

Figure 5:
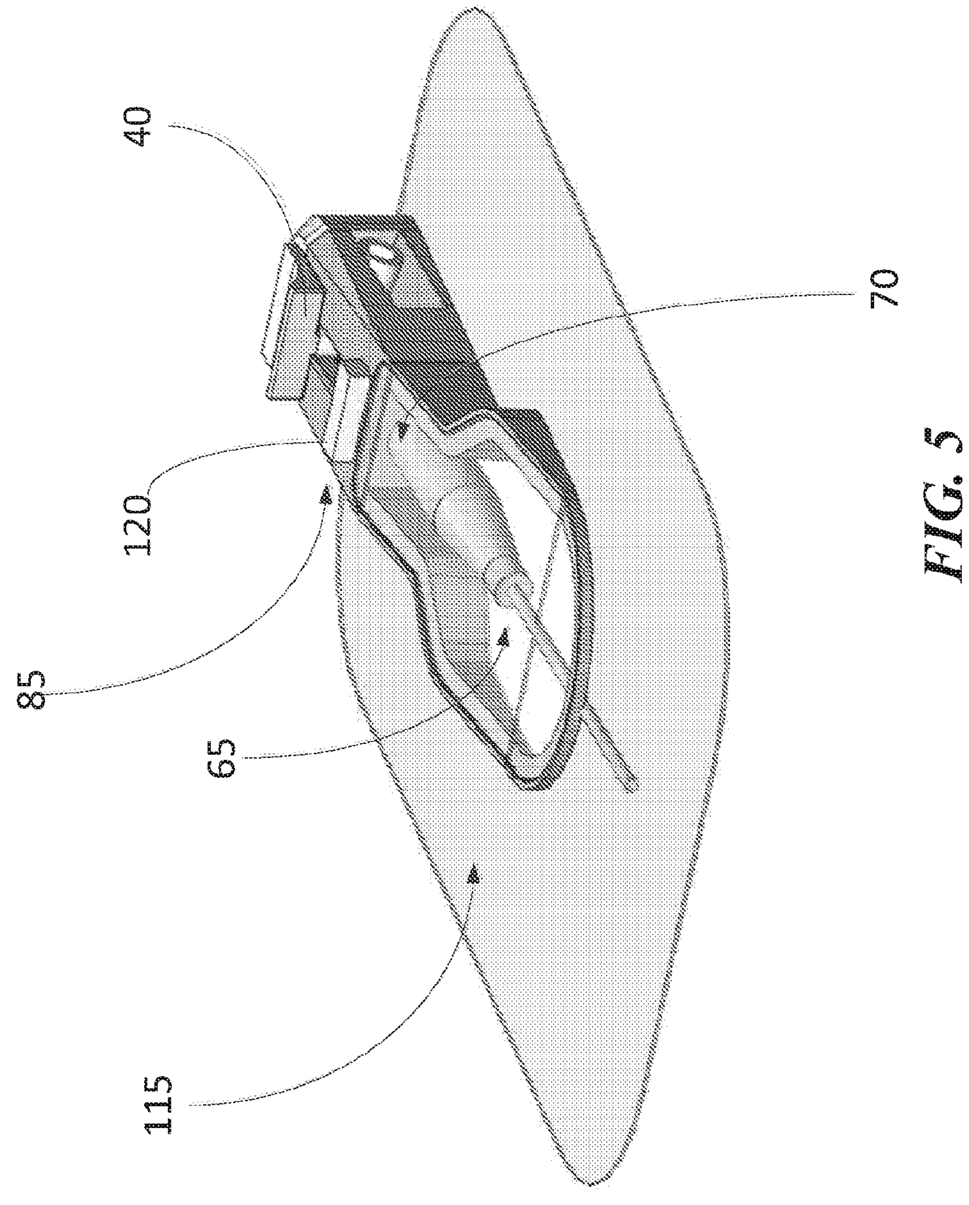
FIG. 5 schematically shows the housing integrated into a dressing (e.g., a patch) in accordance with illustrative embodiments of the invention.

FIG. 5 schematically shows the housing 85 integrated into a dressing 115 (e.g., a patch, such as the patch described in U.S. patent application Ser. Nos. 14/408,436, 14/802,270, 15/367,726, and 15/367,759, all of which are incorporated herein by reference) in accordance with illustrative embodiments of the invention. In this figure, the housing 85 is coupled top-down and/or bottom-up (i.e., transverse to the central axis 75) with the female luer connector 70. When the female luer connector 70 is coupled to the housing 85, the stop 120 is dislodged from its previous position and becomes disengaged. Accordingly, the male luer connector 40 is inserted into the female luer connector 70 to form a fluid connection.

Figure 6:
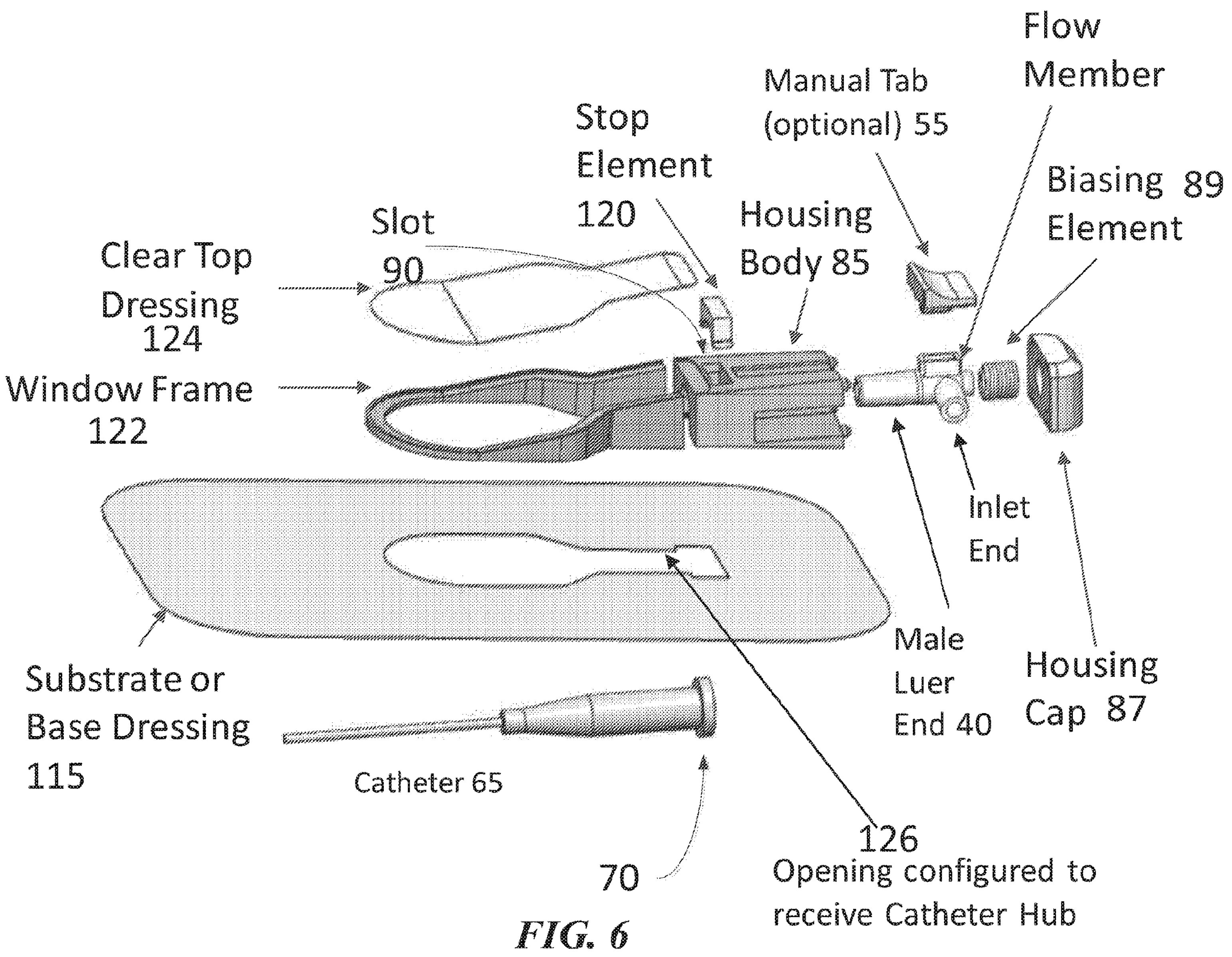
FIG. 6 schematically shows an exploded view of the dressing and the housing of FIG. 5.

FIG. 6 schematically shows an exploded view of the dressing 115 and the housing 85 in accordance with illustrative embodiments of the invention. The catheter 65 is inserted into the patient 30 prior to applying to dressing 115. Thus, applying the dressing 115 including the male luer connector 40 in a top-down orientation provides considerable advantages to the practitioner 20, including easy one-handed connection. Furthermore, no folding or rolling of the patch 115 is required to make the connection.

The dressing 115 may include a window frame 122 including a clear top dressing 124. The clear top dressing 124 allows the practitioner 20 to see the catheter 65 insertion site (e.g., to confirm that the catheter 65 is still in place and/or inserted correctly). In order to be placed over the catheter 65, the dressing 115 may also have an opening 126 that is configured to receive the catheter 65.

The housing 85 may include a housing cap 87 that presses against a biasing element 89. The male luer connector 40 within the housing 85 may be biased by the biasing element 89 while it rests within the housing 85. The biasing element 89 may press against the housing cap 87. Thus, when the housing 85 (e.g., slot 90) receives the catheter 65, the stop 120 is disengaged, and the male luer connector 40 is biased forward by the biasing element 89. In some embodiments, the thumb plate 55 may also be used to assist with forming the fluid connection.

Figure 7:
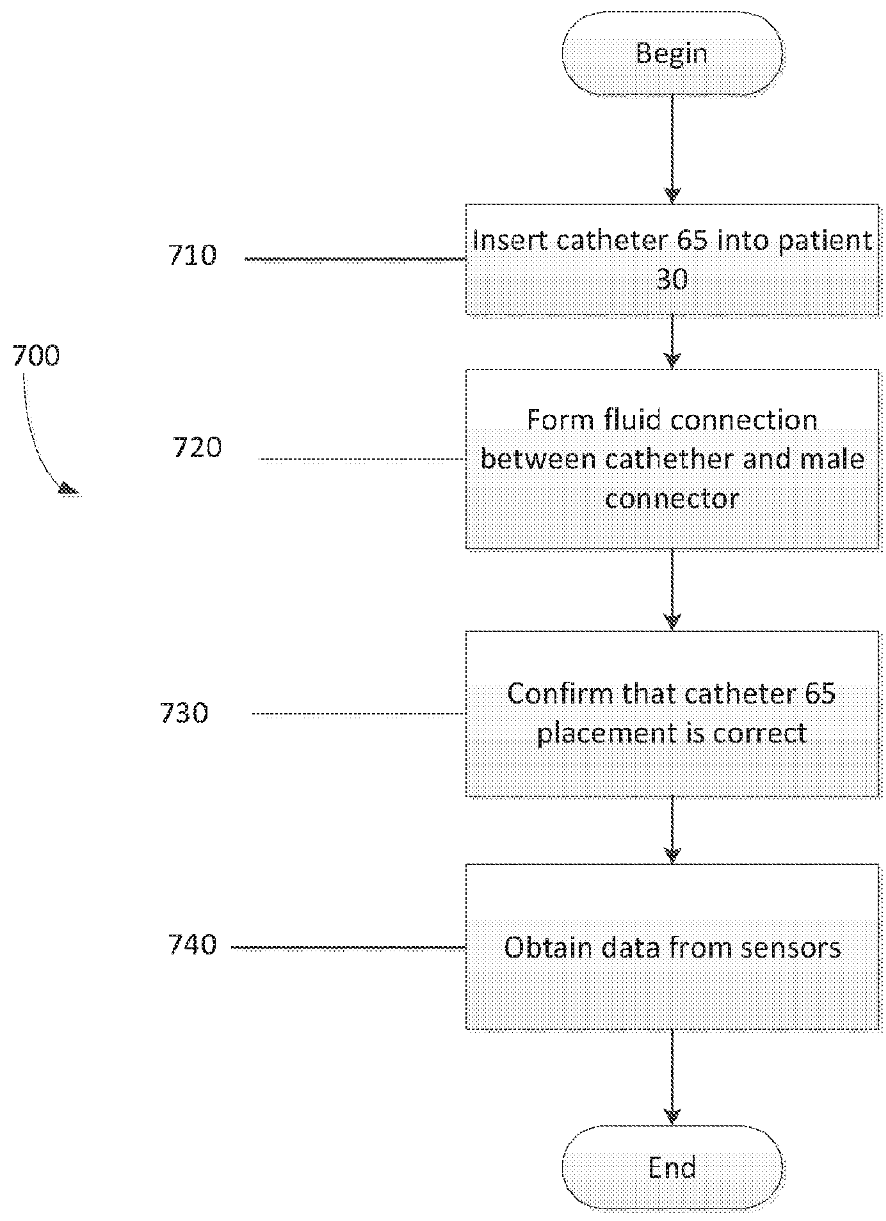
FIG. 7 shows a process of using the housing in accordance with illustrative embodiments of the invention.

FIG. 7 shows a process 700 of using the housing 85 in accordance with illustrative embodiments of the invention. It should be noted that this process is substantially simplified from a longer process that normally would be used.

Accordingly, the process may have many steps that those skilled in the art likely would use. In addition, some of the steps may be performed in a different order than that shown, or at the same time. Those skilled in the art therefore can modify the process as appropriate. The process begins at step 710, where the medical practitioner 20 inserts the catheter 65 into the patient 30. As described previously, there are a number of medical procedures that could require the insertion of the catheter 65.

The process then moves to step 720, where a fluid connection is formed between the female luer connector 70 of the catheter 65, and the male luer connector 40. The male luer connector 40 may be connected to, for example, IV tubing 60 which is in turn connected to an IV bag 50. To form the fluid connection, the housing 85 is coupled with the female luer connector 70. To that end, the housing 85 may be applied independently to the female luer connector 70, or it may be applied as part of a dressing/patch.

Figures 8A, 8B, 8C:
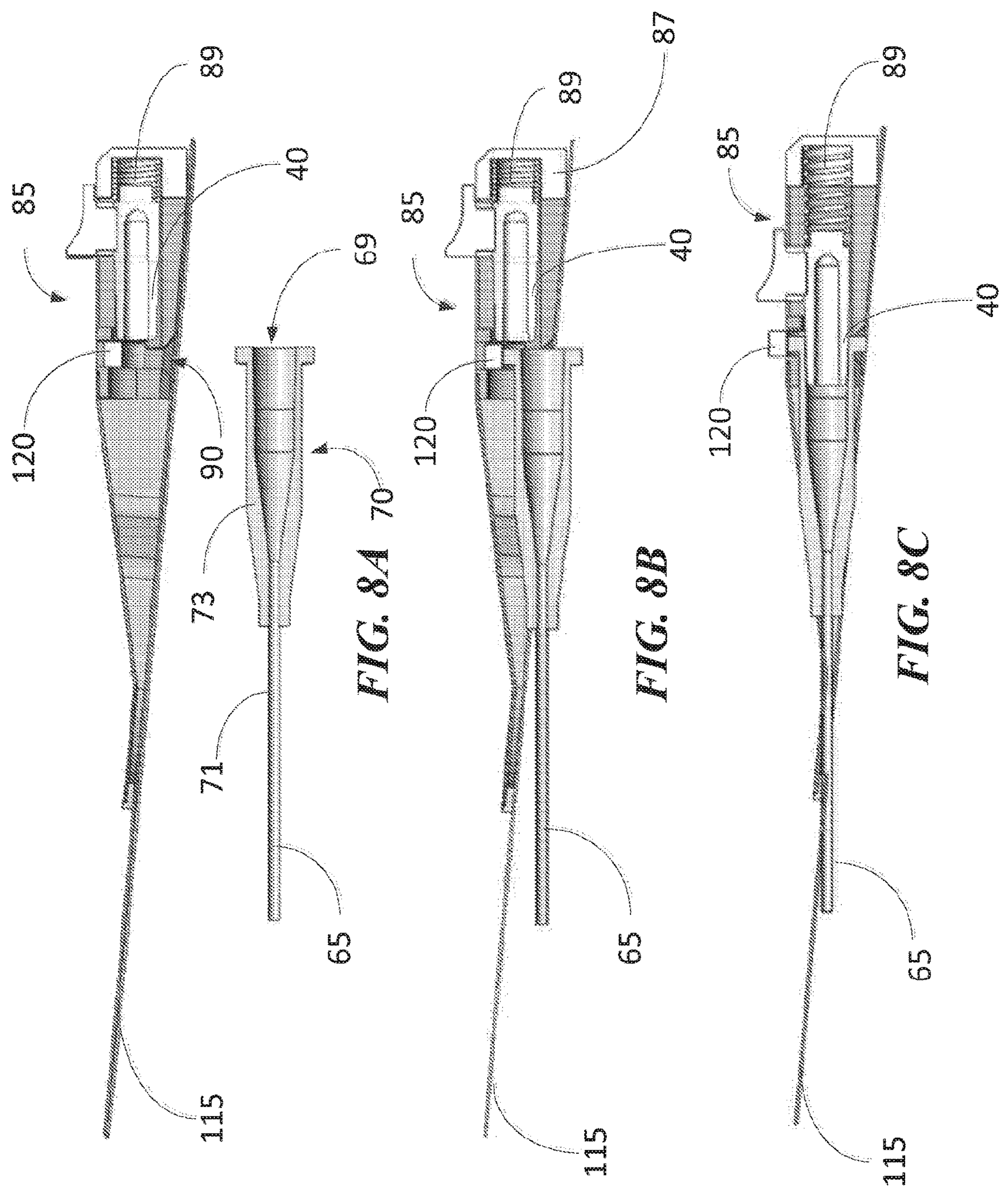
FIGS. 8A-8C schematically show a process of coupling the catheter with the housing in accordance with illustrative embodiments of the invention.
Figure 9:
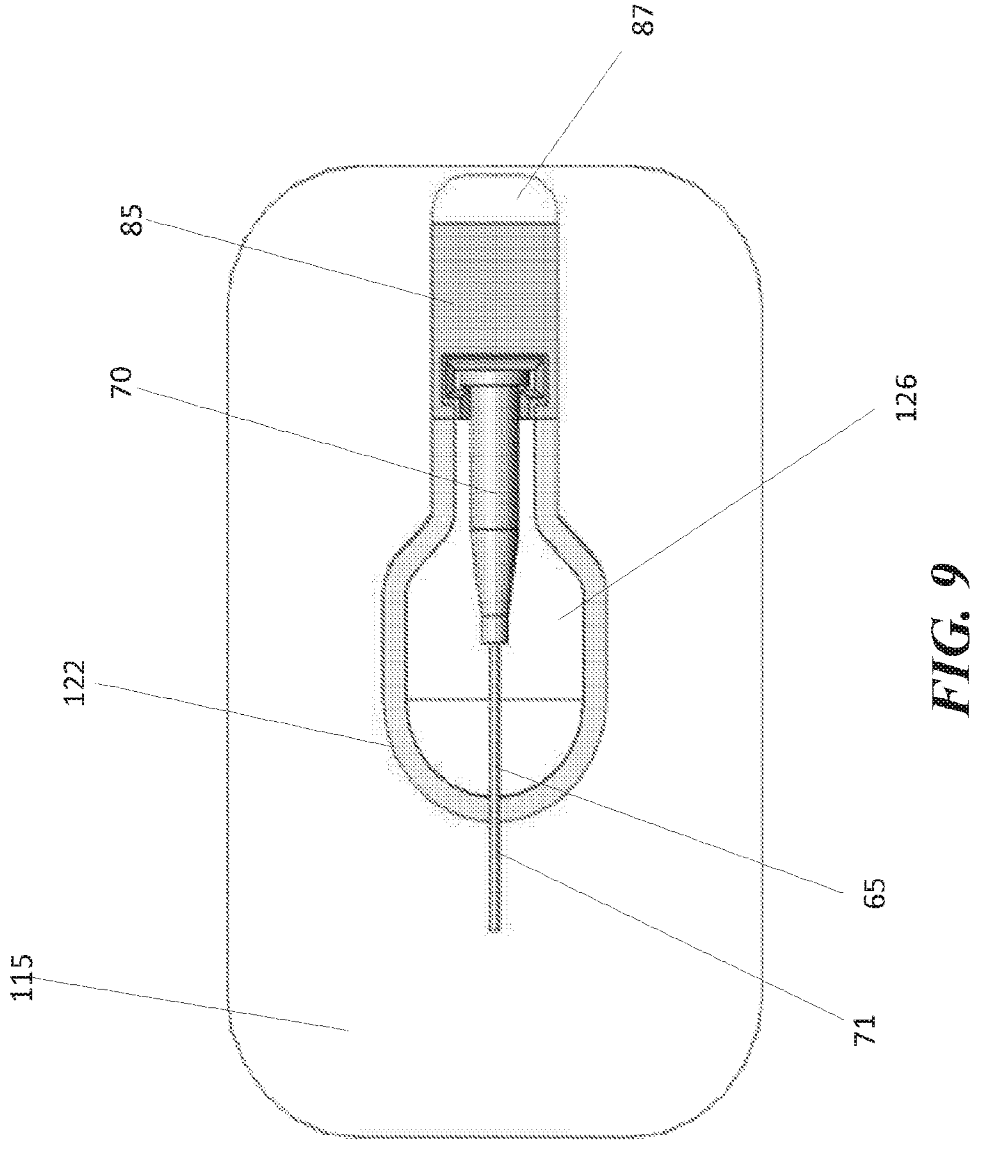
FIG. 9 schematically shows a bottom view of the patch aligned with the catheter in accordance with illustrative embodiments of the invention FIG. 10 schematically shows a patch having electronic sensors on it (e.g., EMG sensors and/or blood sensors) in accordance with illustrative embodiments of the invention.

FIGS. 8A-8C schematically and graphically show a process of coupling the catheter 65 with the housing 85 in accordance with illustrative embodiments of the invention. In FIG. 8A, the housing 85 is coupled with the male luer connector 40. In illustrative embodiments, the housing 85 and the male luer connector 40 may be packaged for the practitioner as an assembled kit (e.g., with the male luer connector 40 pre-biased by the biasing element 89). To couple the housing 85 and the catheter 65, the two are aligned. Specifically, the slot 90 is aligned with a portion of the female luer connector 70. FIG. 9 schematically shows a bottom view of the patch 115 aligned with the catheter 65 in accordance with illustrative embodiments of the invention.

As shown in FIG. 8A, the male luer connector 40 is in the retracted position 105, because the biasing element 89 cannot advance the male luer connector 40 beyond the stop 120. As the dressing/patch 115 is applied to the skin of the patient 30, the practitioner 20 can confirm that the alignment is correct through the clear top dressing 124.

As the dressing/patch is pressed downward, the female luer connector 70 is received in the housing 85. FIG. 8B shows that the female luer connector 70 partially received into the housing 85. The female luer connector 70 begins to make contact with the stop 120. In FIG. 8C, the female luer connector 70 is received into the housing 85, and the stop 120 is disengaged. As a result, the biasing member 89 presses the male luer connector 40 forward and into fluid communication with the female luer connector 70.

Returning to FIG. 7, in the next step 730, the practitioner 20 may optionally confirm that the catheter 65 and/or the patch 115 is positioned correctly relative to the patient 30 (e.g., through the clear top dressing 124). If the catheter 65 and/or the patch 115 is not positioned correctly relative to the patient 30, the practitioner may reposition the catheter 65 and/or patch 115. A portion of the surface of the patch that contacts the patient 30 may optionally contain a skin contacting adhesive that may be covered with a release liner (not shown). The release liner may be removed at any time during the process and the adhesive may have low trauma, repositionable characteristics (e.g., silicone-based) or more permanency (e.g., acrylic). If the catheter 65 and/or patch 115 is positioned correctly, the process 700 optionally proceeds to step 740. In step 740 the patch/dressing 115 may be used to obtain data and/or upload data to a connected device, such as a smart phone (not shown).

Figure 10:
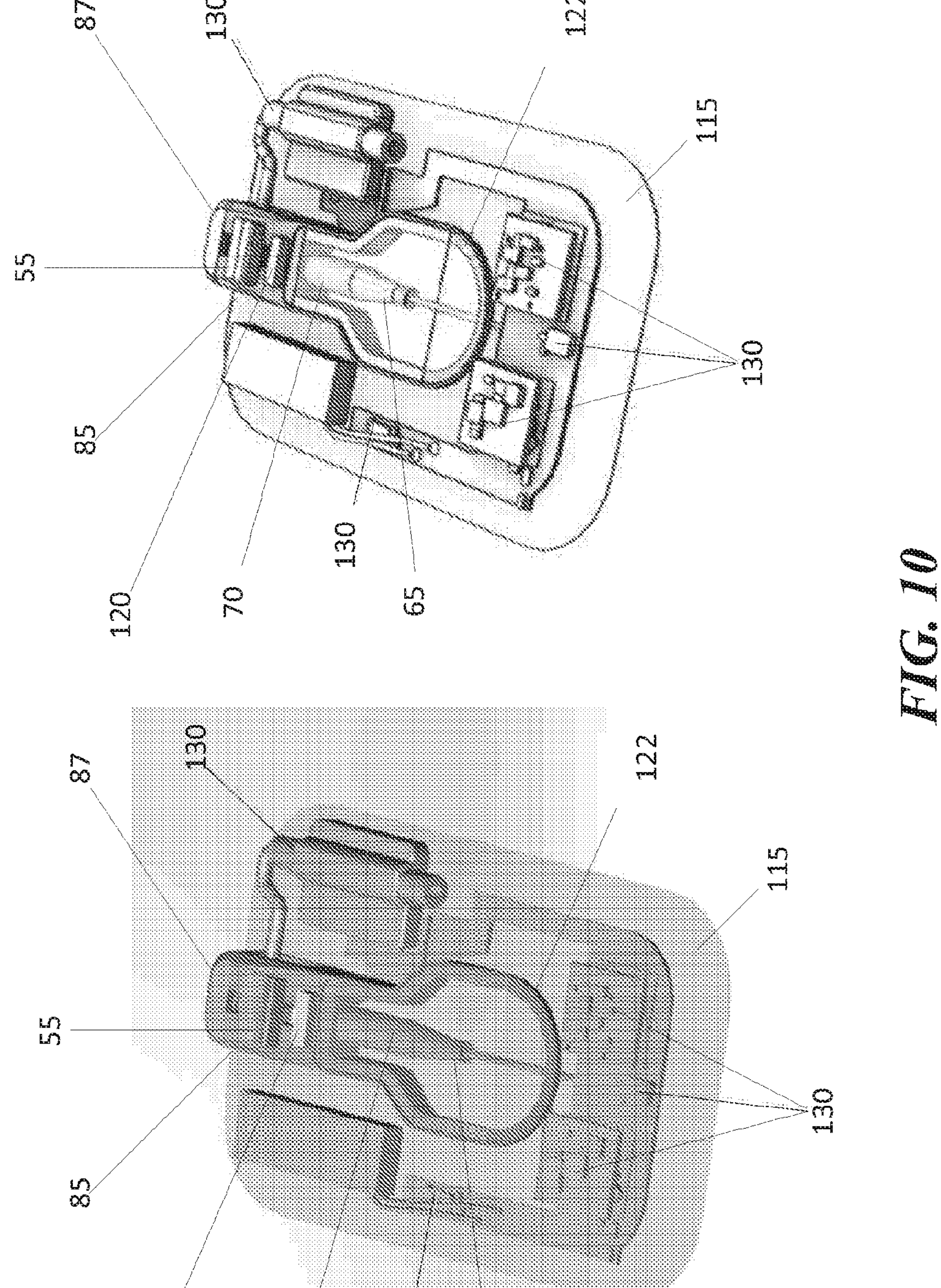

FIG. 10 schematically shows a patch 115 having electronic sensors 130 on it (e.g., EMG sensors and/or blood sensors and/or photoplethysmography sensors, and/or temperature sensors, flow rate sensors, accelerometers, etc.) in accordance with illustrative embodiments of the invention. Data may optionally be obtained at that time, while the male and female luer connectors 40, 70 are coupled. Because a common datum is established between the housing 85, patch 115, and the catheter 65 having a hub when coupled and a fixed length to the tip of catheter 65 is typically specified by the manufacturer, the position of sensors 130 relative to the tip of the catheter 65 can be controlled, which improves the ability of sensors 130 to reliably detect clinical/patient 30 conditions associated with the catheter 65 (e.g. flow, blockage, infiltration/extravasation, insertion site characteristics such as erythema, cellulitis, etc., etc. The process then comes to an end.

Although the above discussion discloses various exemplary embodiments of the invention, it should be apparent that those skilled in the art can make various modifications that will achieve some of the advantages of the invention without departing from the true scope of the invention.

What is claimed is:

1. A system for fluidly connecting a male luer connector and a female luer connector, the female luer connector configured to be located adjacent or upon a patient, the system having:

the male luer connector, the male luer connector having a guide element; and a housing having a first end and a second end, the housing comprising:

an interior formed by a wall having a track starting nearer to the first end, the track configured to contain at least a portion of the male luer connector, the guide element cooperating with the track to guide the male luer connector along a central axis of the housing from a retracted position to an engagement position, the male luer connector transitioning from the retracted position to the engagement position by moving in a direction that is along the central axis of the housing; and an opening nearer to the second end and located on a bottom of the housing, the opening configured to receive at least a portion of the female luer connector such that movement of the housing toward the patient from a first position toward a second position guides the female luer connector along an axis that is transverse to the central axis of the housing while the male luer connector is in the retracted position, the housing transitioning from the first position to the second position to locate the female luer connector along the central axis of the housing, wherein moving the male luer connector and guide element along the track into the engagement position establishes fluid communication between the male luer connector and the female luer connector.

2. The system as defined by claim 1, wherein movement of the housing toward the second position to locate the female luer connector along the central axis of the housing disengages a stop that prevents the male luer connector from moving into the engagement position.

3. The system as defined by claim 2, further comprising:

a biasing member configured to bias the male luer connector towards the second end so that the male luer connector is biased into fluid connection with the female luer connector when the stop is disengaged.

4. The system as defined by claim 2, further comprising a housing cap, the male luer connector being biased against the housing cap.

5. The system as defined by claim 1, wherein the housing is integrated into a patch or a dressing.

6. The system as defined by claim 5, further comprising biosensors integrated into the patch or the dressing.

7. The system as defined by claim 1, wherein the male luer connector has a push button.

8. A method of fluidly connecting a male luer connector and a female luer connector, the female luer connector configured to be located adjacent or upon a patient, the method comprising:

providing a male luer connector, the male luer connector having a guide element;

providing a housing having a first end and a second end, the housing having:

an interior formed by a wall having a track starting nearer to the first end that is configured to contain at least a portion of the male luer connector by positioning the male luer connector into the track in a direction that is along a central axis of the housing, and an opening nearer to the second end and located on a bottom of the housing, the opening configured to receive at least a portion of the female luer connector by positioning the female luer connector into the opening in a direction that is transverse to the central axis of the housing;

positioning the male luer connector into the track in the direction that is along the central axis of the housing;

moving the housing toward the patient from a first position toward a second position, thereby guiding the female luer connector into the second opening along an axis that is transverse to the central axis of the housing, the housing transitioning from the first position to the second position to locate the female luer connector along the central axis of the housing; and advancing the male luer connector and the guide element along the track into an opening of the female luer connector to form a fluid connection between the male luer connector and the female luer connector.

9. The method as defined by claim 8, wherein the housing further comprising a stop configured to prevent advancement of the male luer connector into the opening of the female luer connector, the method further comprising disengaging the stop by positioning the female luer connector into the second opening in the direction that is transverse to the central axis of the female luer connector.

10. The method as defined by claim 9, further comprising a biasing member configured to bias the male luer connector towards the second end so that the male luer connector is biased into fluid connection with the female luer connector when the stop is disengaged.

11. The method as defined by claim 8, wherein the female luer connector is part of a catheter.

12. The method as defined by claim 11, wherein the catheter is configured to be inserted into a patient prior to fluidly connecting the male luer connector and the female luer connector.

13. The method as defined by claim 8, wherein the housing is integrated into a patch or a dressing.

* * * * *